(12) United States Patent
Maschino et al.

(10) Patent No.: US 6,600,956 B2
(45) Date of Patent: Jul. 29, 2003

(54) CIRCUMNEURAL ELECTRODE ASSEMBLY (75) Inventors: Steve E. Maschino, Seabrook, TX (US); Shawn D. Kollatschny, Pearland, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 09/933,087

(22) Filed: Aug. 21, 2001

(65) Prior Publication Data

US 2003/0040785 A1 Feb. 27, 2003

(51) Int. Cl.[7] ................................................. A61N 1/05
(52) U.S. Cl. ....................................................... 607/118
(58) Field of Search ......................................... 607/118

(56) References Cited

U.S. PATENT DOCUMENTS

| | | | |
|---|---|---|---|
| 4,573,481 A | 3/1986 | Bullara | 607/118 |
| 4,920,979 A | 5/1990 | Bullara | 607/118 |
| 4,940,065 A * | 7/1990 | Tanagho et al. | 607/118 |
| 4,979,511 A | 12/1990 | Terry, Jr. | 600/377 |
| 5,215,089 A | 6/1993 | Baker, Jr. | 600/377 |
| 5,251,634 A | 10/1993 | Weinberg | 600/377 |
| 5,265,608 A * | 11/1993 | Lee et al. | 607/118 |
| 5,351,394 A | 10/1994 | Weinberg | 29/872 |
| 5,531,778 A | 7/1996 | Maschino et al. | 607/118 |
| 5,634,462 A * | 6/1997 | Tyler et al. | 607/118 |

FOREIGN PATENT DOCUMENTS

DE  198 47 446 A1 * 4/2000 ......... A61B/5/0492

* cited by examiner

Primary Examiner—Carl Layno
(74) Attorney, Agent, or Firm—Blank Rome LLP (57) ABSTRACT

An electrode assembly to be installed on a patient's nerve has a thin, flexible, electrically insulating circumneural carrier with a split circumferential configuration longitudinally attached to a lead at the distal end thereof. The carrier possesses circumferential resiliency and has at least one flexible, elastic electrode secured to the underside thereof and electrically connected to an electrical conductor in said lead. A fastener serves to close the split configuration of the carrier to prevent separation from the nerve after installation of the electrode assembly onto the nerve. Tear away webbing secured to adjacent serpentine segments of the lead near the carrier enables the lead to lengthen with patient movements.

20 Claims, 6 Drawing Sheets

CIRCUMNEURAL ELECTRODE ASSEMBLY

BACKGROUND OF THE INVENTION

The present invention relates generally to nerve electrodes, and more particularly to an improved circumferential neural (circumneural) electrode assembly for implantation on and electrical stimulation of selected nerve tissue of a patient, the electrode assembly providing reduced nerve constriction, improved tissue compatibility, and reduced current spread, and being configured and fabricated for ease of implantation.

Circumneural electrodes are generally designed to encompass a portion of a nerve longitudinally to permit electrical stimulation of the nerve. The stimulation may be intended to modulate electrical signals or impulses normally carried by the nerve. Alternatively or additionally, the nerve electrode may be used for sensing electrical signals carried by the nerve. The required installation of the electrode on a nerve for such purposes presents a considerable number of design problems. To provide mechanical stability of the electrode relative to the nerve, and in recognition that the nerve can move relative to the surrounding tissue, a structure that encompasses the nerve is desirable. This type of structure also provides efficiency in minimizing or optimizing the distance between the stimulating electrode and the nerve body. Nerves, however, are sensitive and easily damaged or traumatized by abrasion or stresses caused by subjection to mechanical forces.

From a mechanical perspective, an ideal peripheral nerve electrode has a structure strong enough to resist tensile forces arising from the attached conductor cable, but pliant enough to prevent tension, compression or constriction of the nerve. Tensile forces acting on the electrode should be minimized to prevent excess nerve constriction or to prevent the electrode from dislodging from the nerve. In addition, circumferential electrodes should be designed to fit closely against the nerve, and yet minimize constriction of the nerve attributable to swelling of the nerve inside the electrode structure.

Adverse mechanical forces can be attributable to constriction of the nerve by the circumneural electrode, or to a pull on or torque transmitted to the electrode (and thus, to the nerve) by a lead wire. Or the nerve may atrophy as a consequence of lack of nutritional fluid exchange owing to the close proximity of the electrode. Previously popular cuff electrodes have lost appeal because of their stiffness that often causes nerve damage.

Present-day nerve electrodes have been found difficult to install on the nerve using common surgical tools. In particular, many designs do not lend themselves to placement using endoscopic tools. Also, difficulty is encountered in explanting the electrode, because of tissue in-growth.

U.S. Pat. No. 4,573,481 discloses an implantable helical electrode assembly with a configuration having one or more flexible ribbon electrodes. Each ribbon electrode is partially embedded in a peripheral surface of an open helical dielectric support matrix adapted to be threaded or wrapped around a selected nerve or nerve bundle during surgical implantation of the electrode assembly. The resiliency of the assembly allows it to expand in the event of swelling of the nerve. The electrode's expansion characteristic conceptually allows for implantation on a range of nerve sizes. Its resiliency also allows fluid exchange between the helical coils, and mechanical compliance at its ends. But the electrode is difficult to install on the nerve because the helical configuration must first be unraveled and then re-formed about the nerve. In addition, the open structure of the electrode allows for wide current spread between the anode and cathode, which can cause adverse muscle or external tissue stimulation. Further, this electrode is one of those that is difficult to explant or remove from the nerve due to tissue in-growth into the helical structure. Lastly, the complex spiral shape of the electrode renders it difficult to manufacture, lending it to neither automated manufacturing or molding methods.

An improvement in electrode design is disclosed in U.S. Pat. No. 4,920,979, where a flexible electrode-supporting matrix has two oppositely directed helical portions centrally joined and with free outer ends. The helical portions extend circumferentially at least one turn and up to as much as about two turns. A thin, flexible conductive ribbon is secured to the inner surface to provide multiple electrodes on one or both portions, and a connecting electrical cable couples the electrode array to an electronics package for stimulation and/or sensing. The central passage through the helical portions accommodates a pair of pins that extend from the respective closed legs of a tweezer-like installation tool. When the pins are inserted through the central passage and the legs of the tweezers are opened, the helical portions are spread open to allow the assembly to be slipped over the nerve with the two open-sided portions restrained in a direction generally perpendicular to the length of the nerve. Upon release by withdrawing the pins of the installation tool, the two end portions return to a helical shape to encircle the nerve with their electrode portions conductively contacting the nerve surface. This arrangement simplifies electrode installation and reduces nerve trauma during implantation. However, the particular design exhibits poor mechanical retention properties that render the electrode structure easily dislodged from the nerve during implant.

Thus, the availability of these and other circumneural helical or spiral electrodes has not eliminated problems in installation of the electrode on the nerve or in attachment of the lead wire to the electrode assembly. Conflicting design goals of maximizing mechanical strength for fatigue resistance while minimizing spring constant to allow compliance with the nerve and its movement, must be addressed. It is desirable to improve the strength, durability, flexibility and fatigue resistance of the electrode assembly itself, and as well, to improve the mechanical strength of the electrical connection between the lead conductor and the electrode assembly.

In another prior art implantable lead for nerve stimulation, the lead body comprises an MP35N (cobalt chromium alloy) electrical coil conductor having a helical or spiral electrode assembly at its distal end. The conductor has a biocompatible electrically insulative sheath, and a lead connector at its proximal end for insertion into a mating electrical connector of the implanted signal generator. The electrode assembly includes one or more single turn platinum spiral electrical stimulation ribbon conductors with a 90% platinum/10% iridium alloy wire reinforcing component in the weld between the conductor coil and the ribbon electrode. The ribbon conductor is molded in a silicone elastomer insulating material so that the conductor portion is bonded to the insulation but exposed at the underside of the spiral. An integral anchor tether is employed to retain the implanted electrode in place without undue flexing, thereby substantially reducing the possibility of fatigue and fracture of the electrode or the weld connection to the conductor coil.

In the latter prior art design, heat treating of the platinum ribbon stimulating electrode surface makes the platinum material soft and ductile, creating vulnerability of the ribbon electrode to damage during implantation if subjected to excessive manipulation or improper handling. If the electrode helix is overly stretched by the surgeon during installation of the electrode on the nerve, it may be deformed to an extent that affects its performance and long term reliability as a nerve-stimulating electrode. The tether reduces the magnitude of repetitive, small force loads on the lead connection to the electrode after implantation, but the possibility of mechanical fatigue at the weld joint remains.

The assignee of the invention disclosed in the present application owns several improvement patents covering nerve electrodes, including U.S. Pat. Nos. 4,979,511; 5,215,089; 5,251,634; 5,351,394; and 5,531,778. The '511 patent discloses the feature of a strain relief tether for an implantable nerve electrode. The '778 patent discloses a nerve electrode having a ribbon conductor portion composed of platinum-iridium alloy that is stronger than prior types because it is neither heat treated nor annealed. The electrode is preferably made from a platinum-iridium alloy ribbon rather than reinforcing platinum with another Pt/Ir ribbon since the Pt will anneal from the weld heat. Thinner ribbon improves flexibility and elastic memory of the electrode assembly, allowing the electrode to be opened and placed on the nerve during implantation with greater assurance that, upon closing, it will return to its original shape without distortion. The number of turns of the helix is reduced from 3 to 2-½ to simplify installation of the electrode on the nerve, while maintaining an adequate number of turns for attachment.

In the latter design, the strength of the coil/ribbon weld junction is improved by virtue of the alloy's retention of mechanical strength in the weld area. Both ribbons are 0.013 mm thick, totaling 0.026 mm. Further improvement in the weld junction is achieved by welding the conductor coil of the lead directly to the reinforced ribbon, which improves the mechanical interlocking of the coil and ribbon structure into the silicone elastomer. The effect is to reduce stress transmitted directly from the coil to the ribbon, and prevent separation of the silicone elastomer from inside the welded ribbon area. Silicone elastomer is encapsulated inside a cylinder formed by the ribbon loop, in which the weld area resides. Swelling of the elastomer in body fluids increases mechanical stability inside the weld loop to preclude or minimize tissue in-growth into that area.

The electrode assembly of the '778 patent includes a flexible electrically insulative carrier of helical configuration, a flexible ribbon electrode secured to the underside of at least a segment of the helical configuration, an elongate conductor for electrical connection to the ribbon electrode, and a flexible conducting spacer electrically connected to the ribbon electrode and to the elongate conductor for separating the latter from the helical configuration while maintaining electrical connection between the two at the distal end of the conductor. The distal end of the lead projects directly and tangentially from a curved portion of the spacer in a direction substantially parallel to the longitudinal axis of the helical configuration.

It is a principal aim of the present invention to provide an electrode assembly for nerve stimulation, with improvements in resiliency of its electrode structure to reduce constriction of the nerve, in tissue compatibility, and in reduction of current spread, and which is more easily implanted on the nerve.

Another aim is to provide a nerve electrode assembly that offers improved retention on the nerve while it reduces constriction of the nerve, relative to prior nerve electrodes.

SUMMARY OF THE INVENTION

The present invention provides a nerve electrode design comprising a flexible electrode-supporting matrix that has one or more circumferential metallic electrodes centrally joining a central spine or elongate conductor. Helical portions extend circumferentially up to one turn or 360 degrees. A thin, flexible conductive ribbon is secured to the inner surface of the matrix to provide multiple electrodes on one or both portions, and a connecting electrical cable couples the electrode array to an electronics package for stimulation and/or sensing. One feature of the design is the ability of the electrode to elastically expand along the circumference of the electrode. The flexible conductive ribbon material is connected to a thin resilient material which stretches under small stresses. The ability of the electrode to stretch prevents nerve constriction and nerve damage. The amount of elasticity and expansion needed to accommodate swelling of the nerve can be controlled by material selection and thickness of material. For example, silicone rubber is one material which has good elastic properties. One approach to produce the desired elastic electrode structure is to use a thinly folded material such as polytetrafluoroethylene (PTFE) which will allow for expansion and stretching of the electrode along the circumference. Another approach is to fabricate the electrically conductive element from a conductive fabric made from fibers such as polyester that are sputter coated with a conductive metal coating. Using this approach a conductive, elastic fabric is formed by essentially combining conductive fibers with elastic fibers. The conductive fibers or coating on elastic fibers may be composed of any one of the precious metals or their oxides or alloys thereof, or of carbon or graphite. Conductive elements may also be made of braided or mesh materials.

The electrode may consist of one conductor (monopolar) or any number of conductive elements. To prevent current spread, the electrode has a cuff configuration. The cuff material should be electrically insulating, and possess properties of thinness and resiliency to enable it to conform closely to the shape of the nerve and be less constrictive than current designs, as well as to minimize forces and stress concentrations imparted by it to the nerve. The material is biocompatible and preferably porous, composed, for example, of a polymer such as PTFE or polyester. Or a silicone elastomer may be used, with porosity provided by piercing the material to form small holes in it, typically of a size less than 5 microns. The porous insulation allows for fluid and ion transfer to the nerve, and nourishment and pore size is minimized to prevent tissue ingrowth. Tissue ingrowth into the longitudinal seam is prevented by cuff overlap. Ideally, the insulting material should have viscoelastic properties and the materials elastic modulus should be compatible with the surrounding tissues.

The simple cuff geometry of the nerve electrode design of the present invention offers the advantage of ease of implantation. The electrode can be easily placed onto the nerve endoscopically using common surgical instruments such as miniature forceps. The surgical procedure consists of passing the electrode in a protective cylindrical carrier to a site adjacent to the isolated nerve attachment site. The electrode then is removed from the carrier and grasped on each of the free ends of the electrode structure. The electrode is then placed around the nerve and secured by hooking the fastener. Alternatively, the electrode can be tied together at the ends by using elastic ties. The ties are made from silicone rubber or other resilient material which allows for stretching due to nerve swelling or tensile forces acting on the electrode structure from the cable.

The conductive element is preferably composed of a thin metallic ribbon or small diameter metallic fibers, of an inert material such as one of the platinum group metals or one of its oxides such as iridium oxide or rhodium oxide. The surface area of the electrode is chosen to prevent excessive dissolution, and the electrode is designed to operate within safe charge injection limits for the material chosen. The conductive elements may be cathodes, anodes or any combination of cathode/anode. The conductive elements are preferably spaced apart a distance of at least one diameter to prevent current shunting between the cathode and anode.

A method of reducing tensile forces imparted to the electrode is discussed in the aforementioned '511 patent, but the tether design of that electrode suffers some installation difficulty owing to multiple helical turns. An embodiment of the electrode of the present invention incorporates a service loop built into the coil to absorb stresses from the cable and minimize stress at the electrode structure that is located around the nerve. A feature of the service loop is a thin tear away webbing that extends between adjacent serpentine undulations of the cable to prevent tissue ingrowth therebetween. This creates a planar section which is unobstructed by tissue, and the tear away webbing feature allows the cable to extend, under tensile stresses, by pulling through the tissue. This feature may be incorporated along the lead body to allow for extension of the lead under typical stretching of the lead body which can occur during normal body movements or due to growth of younger patients.

Prior art cuff electrode designs have had a disadvantage of nerve constriction due to swelling of the nerve from trauma of the implantation procedure, which can cause nerve damage. The design afforded by the present invention incorporates a flexible material such as a thin layer of PTFE or fabric material which insulates the metallic conducting elements and minimizes nerve constriction. The circumneural electrode sheath can expand independently from the metallic stimulating electrodes.

Previous cuff electrodes have also suffered from designs that do not allow fluid or ion exchange across the insulator material. This can cause poor ion exchange, electrolyte imbalance, and entrapment of residual by-products due to electrochemical stimulation reactions. The present design incorporates a porous material such as a thin layer of silicone rubber, PTFE or fabric material that insulates the metallic conductors and allows fluid and ion exchange.

Additional advantages of the design of the present electrode include the following:

(i) ease of placement on a nerve with common surgical tools because it does not encircle the nerve for multiple turns, and ease of fixation to the nerve;

(ii) ease of explantation since it only encircles the nerve one revolution and the continuous sheath insulator cuff can be removed in one piece;

(iii) insulated between cathode and anode, so as to limit the stimulus current spread to adjacent tissues;

(iv) readily fabricated using automated manufacturing methods;

(v) incorporates elastic closure ties or straps which are designed to keep the electrode encircled around the nerve but allow for expansion due to swelling;

(vi) circumneural electrode sheath can expand independently from the metallic stimulating electrodes;

(vii) electrode materials selected to match tissue compliance and elastic modulus;

(viii) incorporated medication in or coated surface of electrode to minimize tissue inflammation, improve tissue compatibility, lower stimulation threshold, and/or prevent tissue adhesion;

(ix) electrode structure of woven polymeric fabric incorporates metallic fibers or metallic coating for strength, thinness and elasticity, for conformance to the nerve and matching to tissue modulus and compliance, and prevention of tissue in-growth.

BRIEF DESCRIPTION OF THE DRAWINGS

The above and still further aims, features and attendant advantages of the invention will become apparent from a consideration of the following detailed description of the presently contemplated best mode of practicing the invention, and preferred embodiments and methods thereof, taken in conjunction with the accompanying drawings, in which.

DETAILED DESCRIPTION OF THE PRESENTLY CONTEMPLATED BEST MODE OF PRACTICING THE INVENTION

In the Figures, which are not representations to scale of the depicted embodiments, common reference numbers are applied to common parts. All components of the device which is to be implanted in the human or animal body are biocompatible.

A preferred embodiment of a circumneural electrode assembly 10 according to the present invention is illustrated in FIGS. 1A, 1B, 1C, 2A and 2B. The assembly 10 is of a cuff design arranged or adapted to open along a split 17 in the cuff where it is to be opened to encircle a portion of the nerve for implantation. The electrode assembly includes plural spaced apart electrical conductors 13, 14 and 15 (the number of conductors merely by way of example, and not a limitation) which are connected through the body or matrix 18 of the assembly to a lead 19 or electrical cable that couples the electrode array to an electronics package (e.g., a signal generator) for stimulation and/or sensing. In practice, cable 19 is electrically connected to an implantable or external signal generator (not shown) that supplies stimulating signals to the electrode assembly and thereby to the nerve (not shown), or receives sense signals from the nerve via a sense amplifier in the generator, when the electrode assembly is installed thereon. Lead 19 includes one or more conductors 20 depending on the number of stimulating or sensing functions, or both, to be performed by the generator.

The flexible electrode-supporting matrix 18 has its plural circumferential metallic electrodes as helical portions extending circumferentially at the underside of the matrix up to one turn or 360 degrees. Each electrode conductor (again, a single conductor electrode assembly is contemplated), which may be nominally in the form of a thin, flexible conductive ribbon, is secured to the inner surface of the matrix to provide the multiple electrodes. The assembly body 18 is preferably composed of a polymeric insulation material which is injection molded or otherwise formed to incorporate the conductors 13–15 exposed at its underside and to normally assume its curled, cuff shape. To that end, the body 18 may be a thin layer of silicone rubber or of PTFE, both of which possess good elastic properties for expansion and stretching of the electrode along the circumference. Alternatively or additionally, one or more elastic sections 22 of the body utilizes a resilient fabric, such as of a type discussed in the next paragraph.

This ability of the electrode 10 to elastically expand along its circumference is a feature of the electrode design of the present invention, to prevent nerve constriction and nerve damage The flexible conductive ribbons 13–15 may be connected to a thin resilient material (e.g., the electrode assembly) which stretches under small stresses. Preferably, however, these electrically conductive elements are formed from an elastic or resilient fabric which is braided, meshed or woven from fibers such as polyester, and sputter coated with a conductive metal coating such as any one of the precious metals, or their oxides, or alloys thereof, or of biocompatible conductive materials such as carbon or graphite, or having the conductive metal particles incorporated therein, thereby providing a conductive elastic fabric. Elastic section 22, if used, is formed using only the elastic fabric, without conductive coating or incorporation. Alternative elastic or resilient materials for forming the base material of the conductive ribbons 13–15 or the entirety of the elastic section 22 include polyester, or silicone elastomer with small holes pierced into it.

The insulating material is thin and flexible to minimize stresses to the nerve. Porous insulation enables fluid and ion transfer to the nerve. Pore size of the finished material is minimized to prevent tissue ingrowth. When installed on the nerve, the cuff 10 is fastened closed by inserting projecting clasps 24 into mating holes 25 at opposite sides of the cuff split 17. The overlap of the two sides of the closed cuff at the split is designed to prevent tissue ingrowth into the longitudinal seam. Sutures or ties 26 on one side and corresponding elements 27 on the other side allow alternative closure, or fail-safe closure of the cuff to prevent it from opening even if the clasps should become unloosened from their mating holes. The ties are made from silicone rubber or other resilient material which allows for stretching due to nerve swelling or tensile forces acting on the electrode structure from the cable (lead). Since the cuff body 18 is made of very thin resilient material which conforms to the shape of the nerve and is less constrictive than current designs, the insulating structure of the electrode assembly will impart minimal forces and stress concentrations to the nerve. Preferably, the insulting material possesses viscoelastic properties, and an elastic modulus compatible with the surrounding tissues.

Figure 1A:
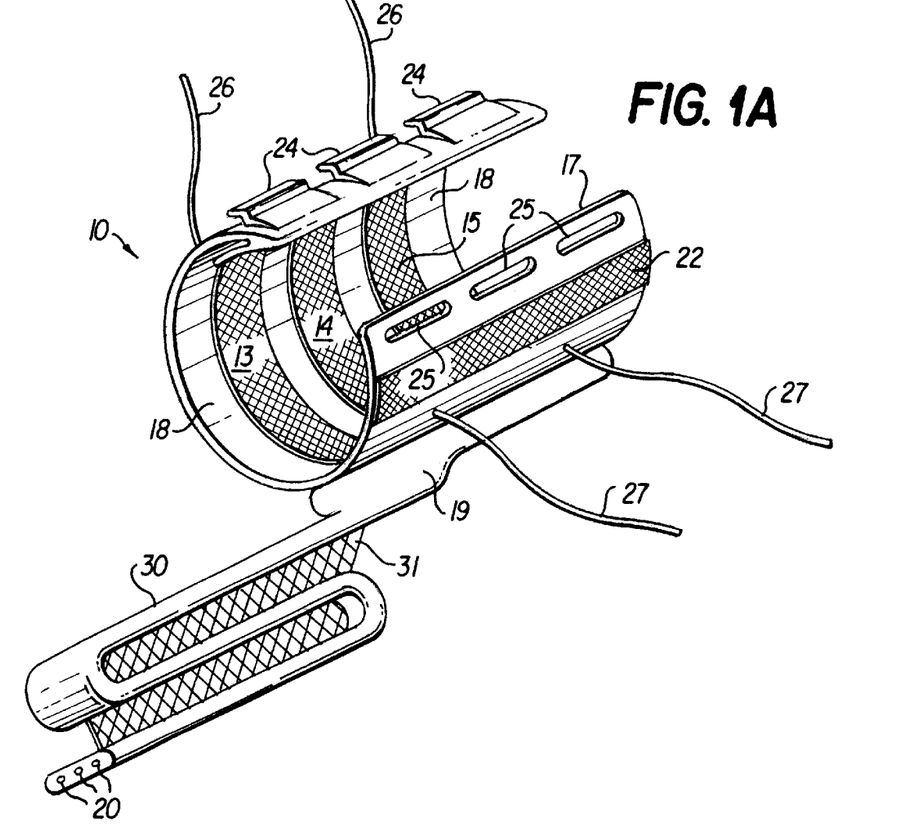
FIGS. 1A, 1B and 1C are respectively a perspective view, an idealized end view, and a detail view of a preferred embodiment of a circumneural electrode according to the present invention.
Figure 1B:
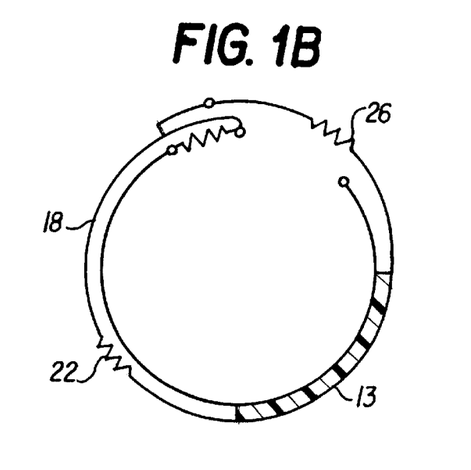
Figure 1C:
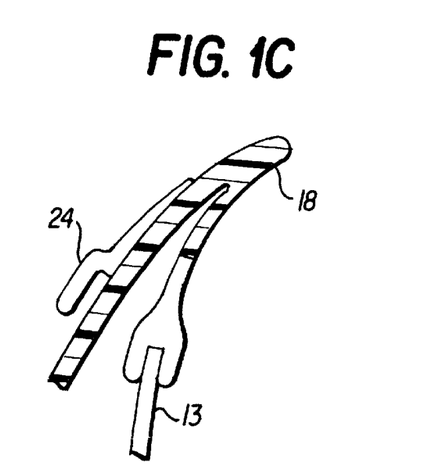
Figures 2A, 2B:
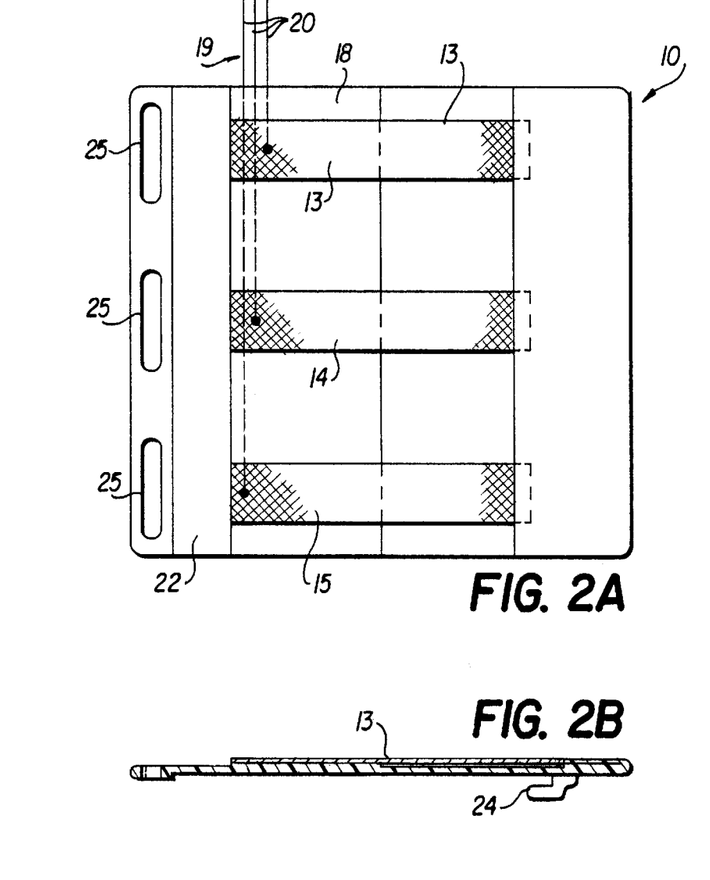
FIGS. 2A and 2B are respectively a flattened view and a side view of the preferred electrode embodiment of FIG. 1A.

A strain relief or service loop 30 is formed along a portion of lead 19 by folding the lead back on itself over a restricted region near the electrode assembly 10, and resiliently fastening the folded regions together with a thin tear away webbing 31. The latter may be the same material as that used for the elastic section(s) of the cuff itself. This built-in strain relief loop absorbs stresses from the cable and minimizes stress at the cuff electrode structure located about the nerve. As noted earlier in the above summary herein, the tear away webbing 31 extends between adjacent serpentine undulations of the lead or cable 19 to prevent tissue ingrowth therebetween. The planar section constituted by this configuration is unobstructed by tissue. Further, the webbing allows the cable to extend, under tensile stresses, by pulling through the tissue. By incorporating the webbing along an extensive portion of the lead, the lead is allowed to extend under stretching that typically occurs with normal body movements, or as a result of normal growth in the case of younger patients.

The simplicity of the cuff geometry design renders the nerve electrode of the invention relatively easy to implant, by placement onto the nerve endoscopically using common surgical instruments, such as miniature forceps. In the surgical implant procedure, the electrode is passed in a protective cylindrical carrier to a site adjacent to the isolated nerve attachment site. At this point, the electrode is removed from the carrier and grasped on each of the free ends of the electrode structure. The electrode is then placed around the nerve and secured by hooking the fastener in the form of the clasps into their mating holes. Additionally, or alternatively, the electrode may be tied or sutured together at its sides by using the ties.

The conductive elements are preferably made of thin metallic ribbon or small diameter metallic fibers, processed in the manner discussed above. Preferably also, inert material such as one of the platinum group metals, or an oxide of the metals of that group, such as iridium oxide or rhodium oxide, is used for the conductive elements. Other important considerations are choice of the surface area of the electrode to prevent excessive dissolution, and electrode operation within safe charge injection limits for the material chosen. The conductive elements may be cathodes, anodes or any combination of cathode/anode, and should be spaced apart a distance of at least one diameter to prevent current shunting between the cathode and anode.

Conveniently, by virtue of the structure and composition of the conductive elements, the nerve electrode of the invention may incorporate a steroid medication on the electrode surface to minimize tissue inflammation and to lower stimulation thresholds. Alternatively, the electrode surface may be coated with polyethylene glycol to improve tissue compatibility. The electrode structure may be coated with a hydrogel to prevent tissue adhesion and thereby ease explant and removal of the electrode assembly. Beyond materials and composition previously described herein for use in the invention, the electrode structure may consist of a woven polymeric fabric that incorporates metallic fibers or metallic coated polymer fibers such as sputtered iridium on polyester fibers to also create a strong, thin, conductive and elastic fabric material so that the electrode conforms to the nerve and may be matched to the tissue modulus. The fabric prevents tissue in-growth into the electrode structure while allowing for fluid penetration and ion transfer to the enclosed nerve tissue.

Figure 3:
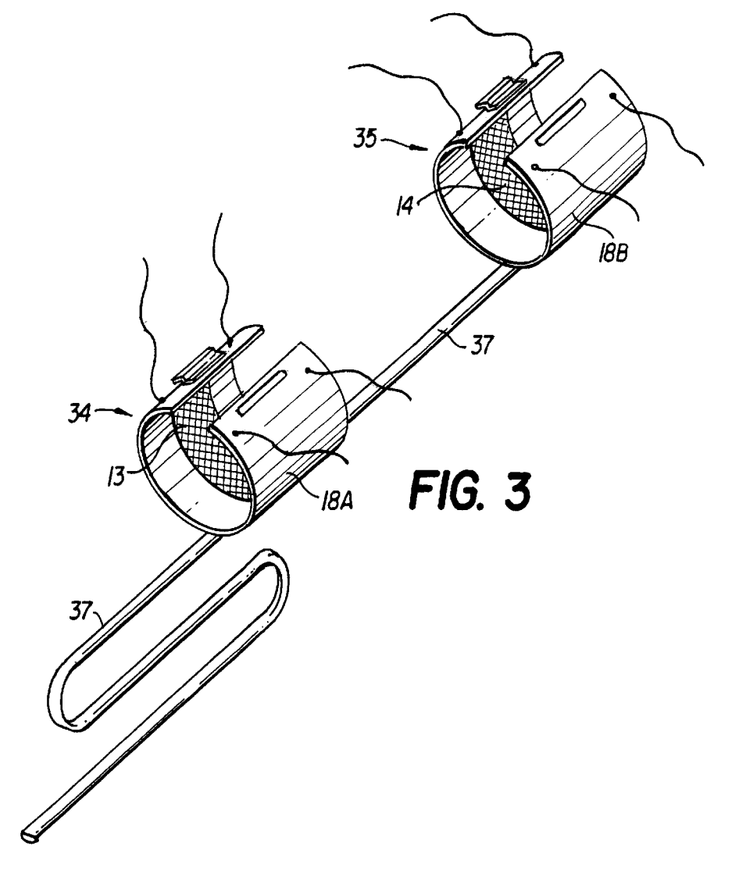
FIG. 3 is a perspective view of an alternate embodiment of a circumneural electrode according to the present invention.

An alternate embodiment of the circumneural electrode of the invention is illustrated in FIG. 3. In this embodiment, a pair of cuff electrodes 34, 35 of the same basic design and construction as that of the preferred embodiment of the preceding Figures is spaced apart and connected centrally along a lead 37 which is molded to or otherwise secured to the two cuff electrodes. The lead acts also as a spine for the configuration. The ribbon electrically conducting elements 13 and 14, in this example, secured at the underside of the respective insulative body 18A, 18B of the cuff electrodes are electrically connected to the conductor(s) within the lead (cable) 37.

Owing to its longitudinal flexibility, this embodiment is especially suited for stimulating and/or sensing electrical activity of the nerve along a greater length thereof, without unduly constricting or abrading the nerve.

From the above disclosure, it will be appreciated that the circumneural electrodes of the preferred and first alternate embodiments possess a unique combination of advantages for stimulating or sensing nerve activity, including ease of implantation and explantation onto and from the nerve, insulation between cathode and anode, ease of fabrication by automated manufacturing methods, incorporating elastic closure ties that keep the electrode encircled around the nerve while permitting expansion of the electrode with nerve swelling, electrode materials that match tissue compliance and elastic modulus, ready acceptance of surface medications either incorporated or coated for reduced tissue inflammation, stimulation threshold and tissue adhesion, and enhanced tissue compatibility, and strength, thinness and elasticity of electrode structure.

In another alternate embodiment, shown in FIGS. 4A, 4B, 4C, 4D, 4E, 5A, 5B, 5C, 6A and 6B, the electrode assembly 50 has two metallic electrodes 56, 57 which are thin ribbon conductors, composed of platinum/20% iridium coated with iridium oxide, about 1.0 mm (millimeter) wide and about 0.005 to 0.010 mm thick, for example, molded into and exposed at the underside 58 (i.e., the surface confronting the nerve, when the electrode is installed) of the electrode assembly's electrically insulating carrier 60. Carrier 60 is composed of silicone elastomer or other insulating polymer integral with or otherwise firmly attached at one edge to spine 52, and unattached (i.e., separated from the spine) at its opposite edge 55. The electrodes 56, 57 may be injection molded or flow molded, for example, into the underside of the carrier 60 during molding of the carrier. The carrier is preferably semi-rigid, i.e., not so flexible that it will not hold its circumferential shape for encircling the nerve when installed thereon, and not so rigid that it is likely to be difficult to open, or likely to abrade the nerve, during installation. The conductors 53, 54 may be electrically attached to the electrodes 56, 57, respectively, at points 61, 62 (FIG. 4B) as by welding, either before or after the molding process, but preferably before so as not to affect the physical characteristics of the carrier 60 in the immediate vicinity of the attachment.

Figure 4A:
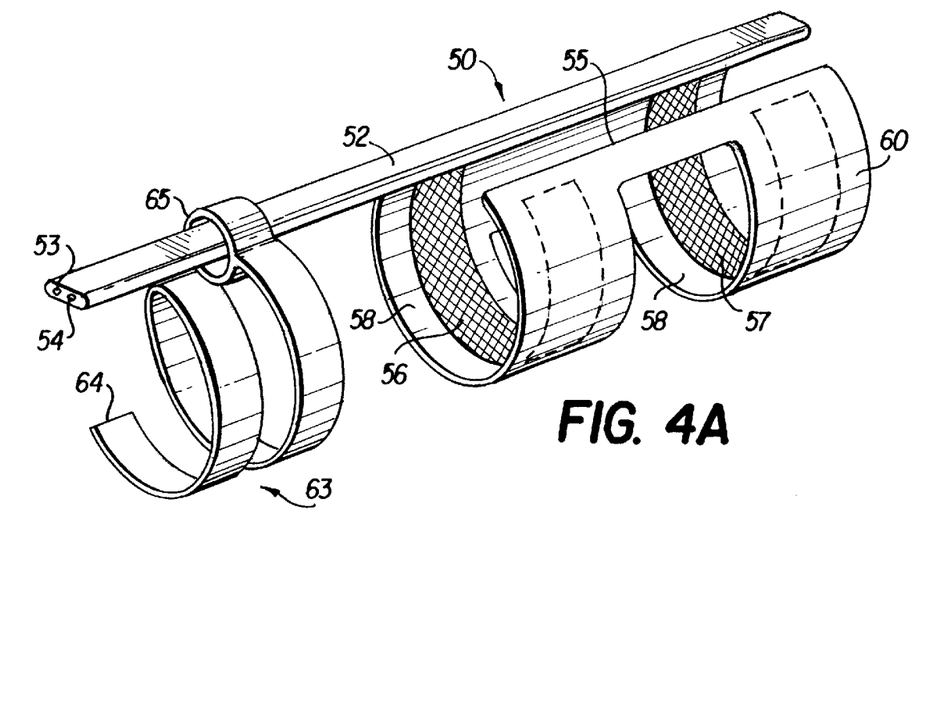
FIG. 4A is a perspective view of another alternate embodiment of a circumneural electrode with tether according to the present invention.
Figure 7A:
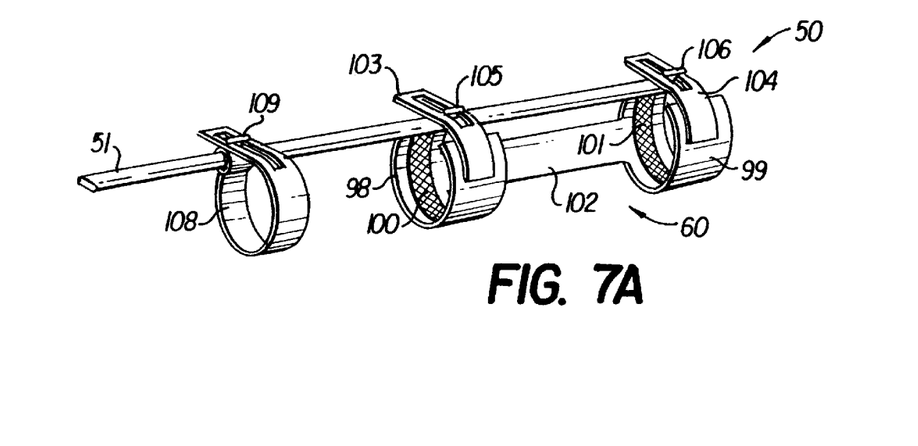
FIG. 7A is a perspective view of another embodiment of a circumneural electrode and tether of the invention.

In this embodiment, electrode assembly 50 has a tether assembly 63, which although shown in the Figure as being helical with more than one turn, may alternatively have a single turn and be circumferential (as shown in FIG. 7A, to be discussed presently). In any event, the tether is open ended (i.e., unattached, at 64) to enable it to be installed about the nerve, and at its other end 65 is preferably rotatably secured to the spine 52 of the electrode assembly 50 to avoid binding or twisting on the nerve. Tether 63 is also composed of a semi-rigid insulating polymer in this embodiment.

Figure 4B:
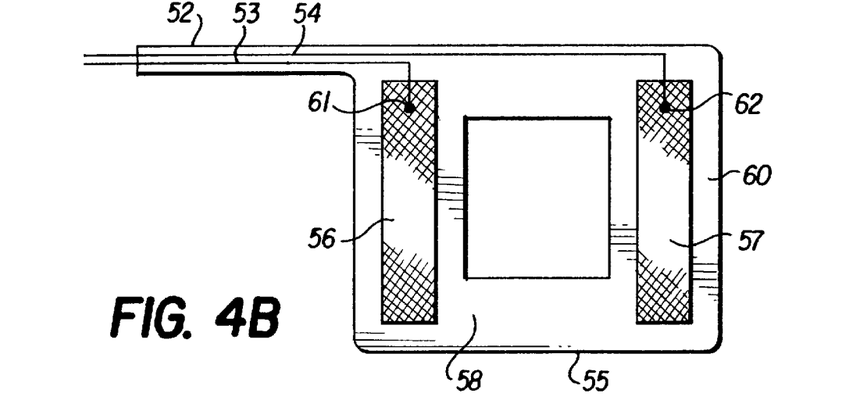
FIGS. 4B, 4C, 4D and 4E are opened, flattened views of various designs of the electrode of FIG. 4A.
Figure 4C:
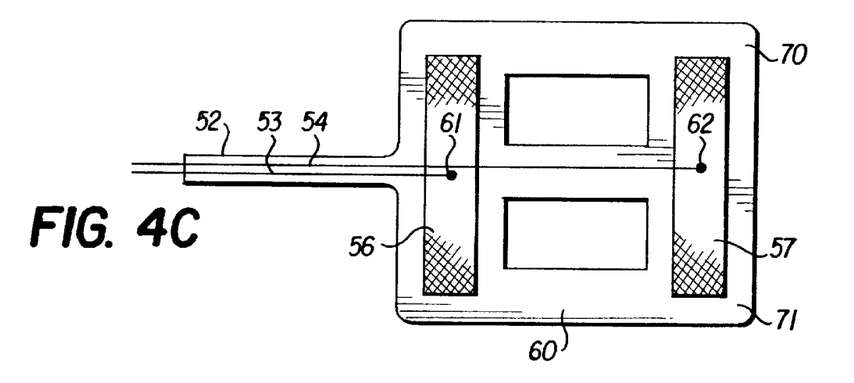
Figure 4D:
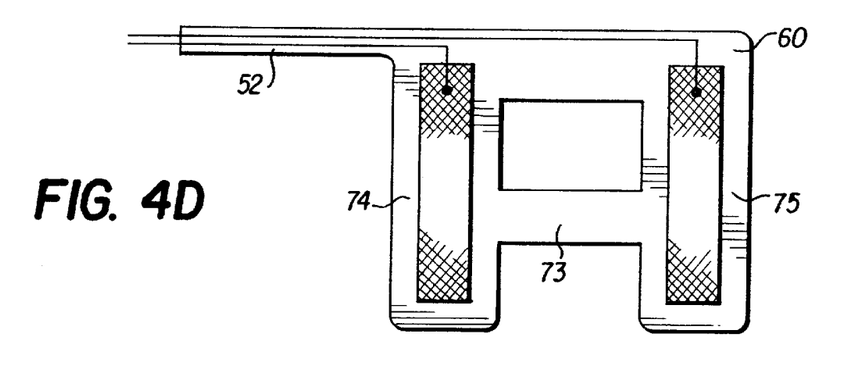
Figure 4E:
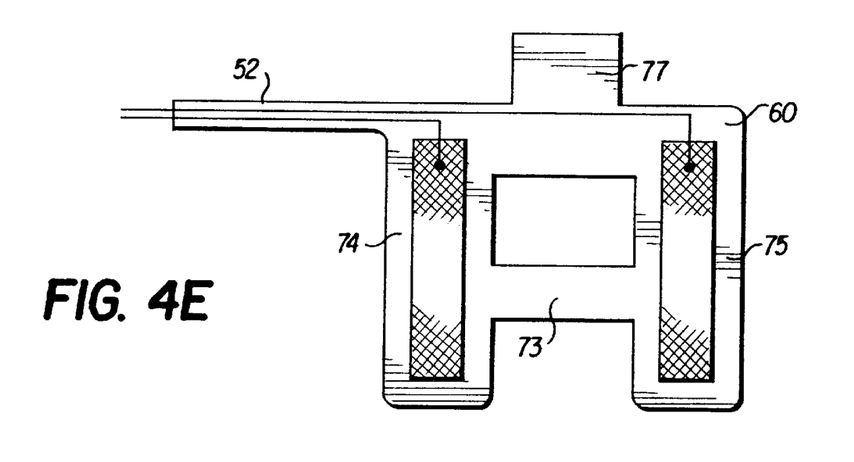

Electrode carrier 60 is curled (to fit comfortably about the nerve) and has the shape of a rectangular loop as shown in FIGS. 4A and 4B (illustrated as opened and flattened), with the ribbon conductors 56, 57 in opposite sides of the loop. Alternatively, the carrier 60 may have an alternative design such as one of those shown in the opened, flattened views of FIGS. 4C, 4D or 4E. In FIG. 4C, the electrode carrier 60 extends symmetrically from the spine 52 in the shape of twin rectangular loops 70, 71, unattached except through the spine, with electrodes 56, 57 centrally attached to conductors 53, 54 at points 61, 62, respectively. The combined width of twin loops 70, 71 extending from spine 52 is substantially equivalent to the width of the rectangular loop of the carrier 60 of FIG. 4B, for encirclement of the nerve in the carrier's normally curled condition. In FIG. 4D, the carrier 60 is of similar shape to that of FIG. 4B, except that the remote (from spine 52) bridging portion 73 between legs 74, 75 is at approximately the middle rather than the remote end thereof. And in FIG. 4E, the shape of the electrode carrier 60 is the same as that of FIG. 4D, with the addition of a tab 77 projecting from spine 52 in the direction opposite from and substantially centrally of the carrier to fasten into the opposing electrode structure.

Figure 5A:
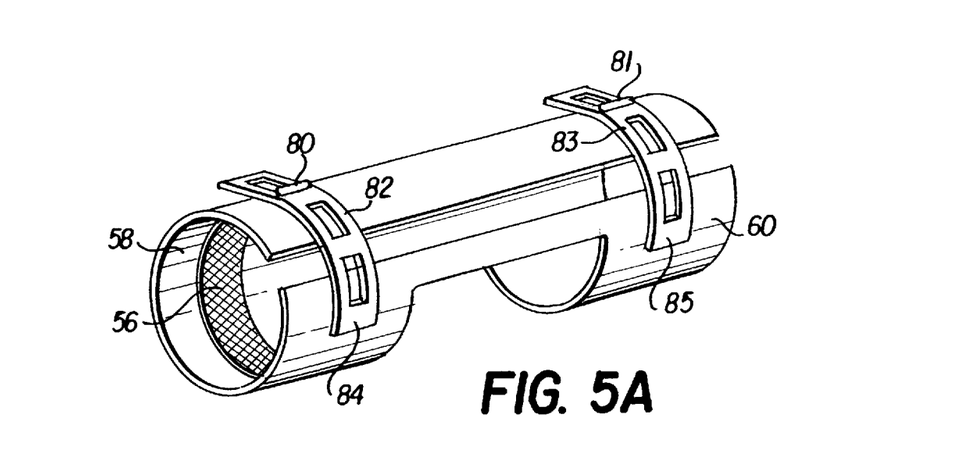
FIGS. 5A, 5B and 5C are perspective views of the electrode of FIG. 4A illustrating various alternative designs for securing the electrode to the nerve.
Figure 5B:
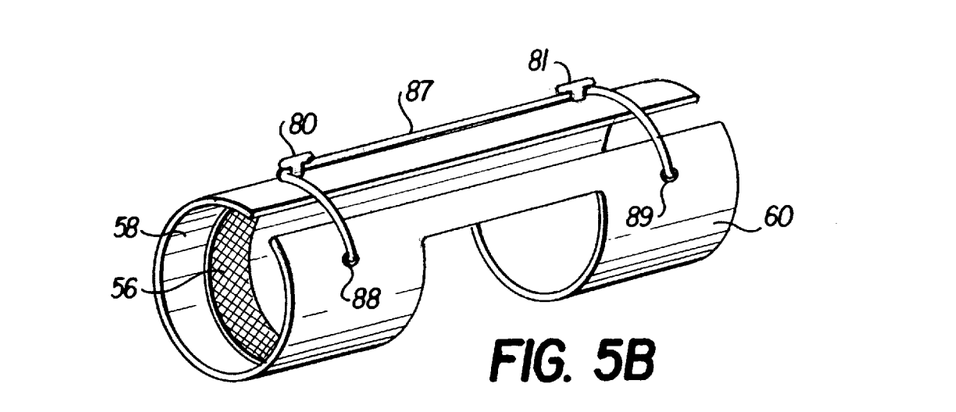
Figure 5C:
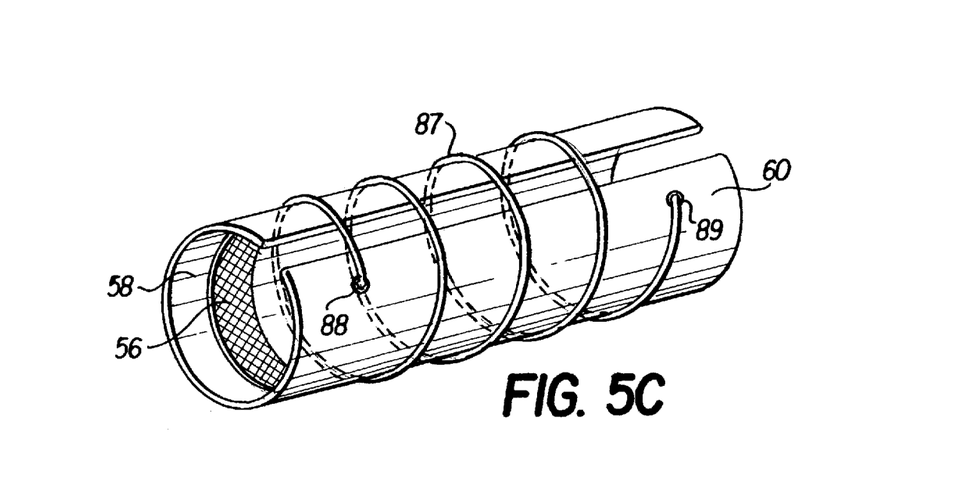

FIGS. 5A, 5B and 5C illustrate various techniques for securing the electrode carrier 60 about a nerve on which it is installed. As shown in FIG. 5A, the carrier may be provided with a pair of spaced-apart clasps or other fasteners 80, 81 adjacent an edge of the carrier that is either attached or unattached to the spine (not shown in this Figure). Fasteners 80, 81 are utilized to fasten an end of respective ones of a pair of flexible or elastic straps 82, 83 secured at the other end (e.g., using a medical grade adhesive) 84, 85 to the opposite edge of carrier 60. After installing the electrode assembly with related lead on the nerve, the implanting physician pulls each strap to a point at which it is fastened to the respective clasp so that the carrier 60 is comfortably spaced apart from the nerve but in electrical communication therewith, and removes the excess material of the straps.

In the embodiment of FIG. 5B, a single flexible or elastic tube or string 87 is used in place of the pair of straps of the previous embodiment. The two ends of string 87 are attached to the carrier 60 at its underside 58 through spaced-apart holes 88, 89 in the wall of the carrier adjacent its edge opposite that at which the clasps are attached, using either medical grade adhesive or by knotting the ends of the string. The attached string 87 is then pulled tightly over the clasps 80, 81 to secure the electrode assembly after installation on the nerve.

In the embodiment of FIG. 5C, the flexible or elastic string 87 is sufficiently long to be wrapped about the electrode carrier 60 after installation of the latter on the nerve. The loose end of the string (fastened at its other end at hole 88 or 89) is then tied off at the other hole, on the underside 58 of carrier 60.

Figure 6A:
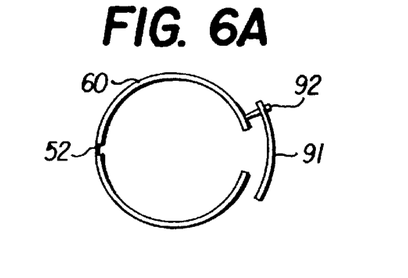
FIGS. 6A and 6B are end views of the electrode of FIG. 4A using alternative designs for securing the electrode to the nerve.
Figure 6B:
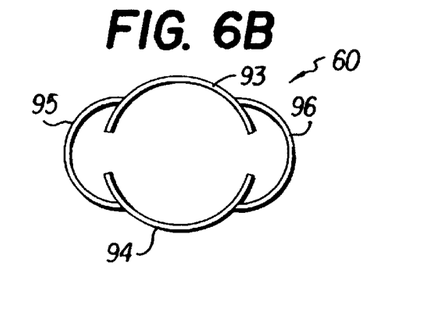

In the embodiment of FIG. 6A, viewed from an end of the electrode carrier 60, which has a configuration similar to that shown in FIG. 4C, the carrier is effectively hinged along the spine 52. Flexible strap 91, similar to that of 84 and 85 in FIG. 5A, is one of a pair that serves in the same manner in conjunction with clasps 92 to secure the carrier 60 onto the nerve. FIG. 6B shows an end view of an embodiment of the carrier 60 that includes two symmetrical "halves" 93, 94, each with an electrically insulating polymer and ribbon electrodes (not shown) molded into its underside. The two halves are secured together over the nerve during installation by a flexible or rigid strap 95 constituting a permanent hinge between the two, and a flexible or elastic strap 96 which is secured in the aforementioned manner after the electrode carrier 60 is placed over the nerve.

Figure 7B:
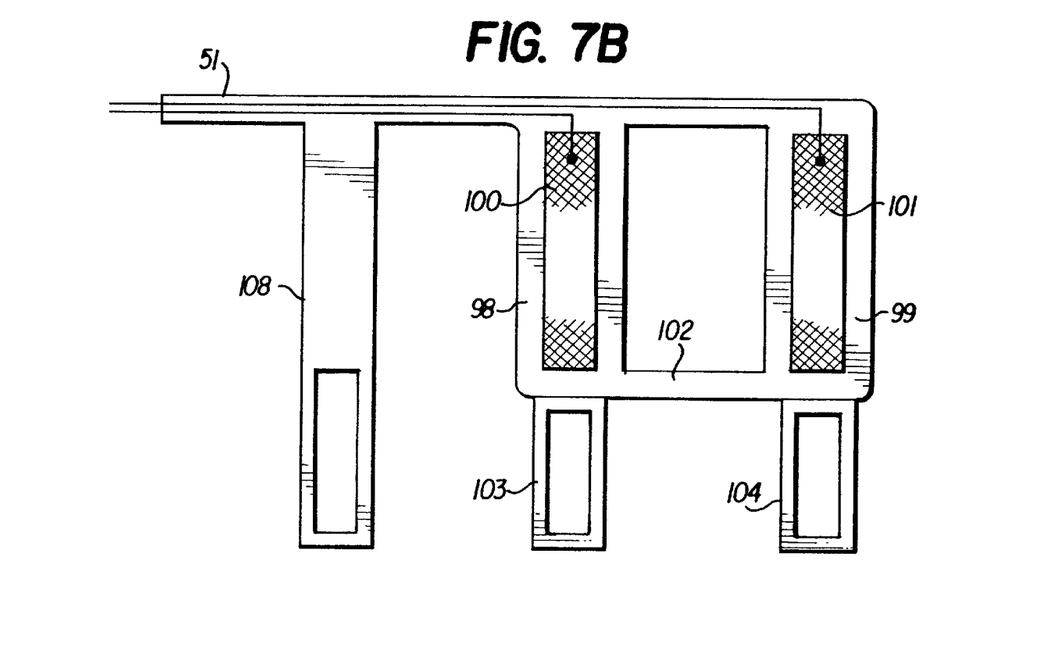
FIG. 7B is an opened, flattened view of the electrode and tether of FIG. 7A.

In addition to the security afforded by various means described herein for securing the electrode carrier 60 about the nerve, a tether is used such as component 63 shown in FIG. 4A to retain the electrode assembly 50 on the nerve. FIGS. 7A and 7B illustrate an embodiment of the electrode assembly 50 in which lead 51 has an electrode carrier 60 at its distal end, the carrier including a pair of curled insulating polymer strips 98, 99, each having a respective ribbon electrode 100, 101 molded into and exposed at its underside. A suitable bridging portion 102 of the same polymeric material connects the two strips 98, 99 together to maintain their spaced apart relationship on lead 51. Elastic strips 103, 104 and respective clasps 105, 106 are mounted and used as described above to secure the electrode carrier onto the nerve during installation. An elastic strip 108 rotatably mounted on the lead 51 is used together with an associated fastener 109 on the mounting as added security to tether the electrode assembly 50 to the nerve after implantation.

In practice, stimulating or modulating signals are applied to the nerve via the electrodes of assembly 50, and intrinsic nerve signals are detected by the electrodes of the assembly for processing in sense circuitry, by the signal generator.

Although a presently contemplated best mode and method of practicing the invention, including certain presently preferred embodiments thereof, have been described in this specification, it will be apparent to those skilled in the art from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An electrode assembly for a lead to be installed on a patient's nerve, comprising:
   a thin, flexible, electrically insulating circumneural carrier having a split circumferential configuration longitudinally attached to said lead at the distal end thereof, said carrier possessing circumferential elasticity,
   at least one flexible, elastic electrode secured to the underside of said carrier and electrically connected to an electrical conductor in said lead, said at least one electrode being composed of electrically conductive fibers, and
   a fastener for closing the split configuration of die carrier to prevent separation from the nerve after installation of the electrode assembly onto the nerve.

2. The electrode assembly of claim 1, wherein:
   said fibers are coated with electrically conducting material to render them electrically conductive.

3. The electrode assembly of claim 1, wherein:
   said at least one electrode is composed of stretchable or non-stretchable fibers having electrically conducting material incorporated therein.

4. The electrode assembly of claim 1, wherein:
   said electrode is coated with an agent to minimize tissue inflammation and lower stimulation thresholds.

5. The electrode assembly of claim 1, wherein:
   said electrode is coated with an agent to enhance tissue compatibility.

6. The electrode assembly of claim 1, wherein:
   said electrode is coated with an agent to prevent tissue adhesion to the electrode.

7. An electrode assembly for a lead to be installed on a patient's nerve, comprising:
   a thin, flexible, electrically insulating circumneural carrier having a split circumferential configuration longitudinally attached to said lead at the distal end thereof, said carrier possessing circumferential elasticity,
   at least one flexible, elastic electrode secured to the underside of said carrier and electrically connected to an electrical conductor in said lead,
   a fastener for closing the split configuration of the carrier to prevent separation from the nerve after installation of the electrode assembly onto the nerve, and
   a tether coupled to said lead adjacent said carrier for additionally securing said carrier and said lead to the nerve after installation of the electrode assembly onto the nerve, said tether comprising a circumferential loop having one end rotatably coupled to said lead and another end free of attachment, and a fastener affixed to the rotatable coupling for engaging the free end of the tether for securing the tether about the nerve.

8. An electrode assembly for a lead to be installed on a patients nerve, comprising:
   a thin, flexible, electrically insulating circumneural carrier having a split circumferential configuration longitudinally attached to said lead at the distal end thereof, said carrier possessing circumferential elasticity,
   at least one flexible, elastic electrode secured to the underside of said carrier and electrically connected to an electrical conductor in said lead, and
   a fastener for closing the split configuration of the carrier to prevent separation from the nerve after installation of the electrode assembly onto the nerve,
   said lead including webbing secured between at least some adjacent serpentine segments of the lead to enable lengthening of the lead in response to movements or growth of the patient's body.

9. The electrode assembly of claim 8, wherein:
   said webbing is of tear away construction.

10. A cuff electrode for implantation on a nerve of the body, comprising:
    a resilient curved split electrically insulating cylinder,
    an elastic electrode secured to the underside of said resilient cylinder between the split therein, and
    an electrically conductive lead secured generally axially along and to the outside of said resilient cylinder between the split therein, said electrode being electrically connected to said lead.

11. The cuff electrode of claim 10, wherein:
    said resilient cylinder has an elastic strip extending longitudinally between the ends thereof.

12. The cuff electrode of claim 10, wherein:
    said resilient cylinder is composed of elastic material.

13. The cuff electrode of claim 10, wherein:
    said lead includes webbing secured between adjacent serpentine segments of the lead at least proximate said resilient cylinder to enable lengthening of the lead in response to movements or growth of the body.

14. An electrode assembly for a lead to be installed on a patient's nerve, comprising:
    a thin, resilient, curled electrically insulating carrier having a spilt circumferential configuration longitudinally attached to and projecting generally perpendicularly from said lead at the distal end thereof,
    at least one resilient ribbon electrode secured to the underside of said carrier and electrically connected to an electrical conductor in said lead, and
    a selectively separable fastener for securing the split configuration of the carrier together to prevent separation from the nerve after installation of the electrode assembly onto the nerve, said split circumferential configuration comprising:
- a curled rectangular loop attached at one edge to said lead, and having an edge opposite said one edge unattached to said lead, and
- a pair of resilient ribbon electrodes, including said at least one electrode, secured to respective spaced apart legs of said rectangular loop projecting perpendicularly from said lead.

15. An electrode assembly for a lead to be installed on a patient's nerve, comprising:
- a thin, resilient, curled electrically insulating carrier having a split circumferential configuration longitudinally attached to and projecting generally perpendicularly from said lead at the distal end thereof,
- at least one resilient ribbon electrode secured to the underside of said carrier and electrically connected to an electrical conductor in said lead, and
- a selectively separable fastener for securing the split configuration of the carrier together to prevent separation from the nerve after installation of the electrode assembly onto the nerve,
- said split circumferential configuration comprising:
  - a pair of spaced apart curled rectangular strips attached at one edge to said lead and having an edge opposite said one edge unattached to said lead, and a bridge connection between said pair of strips to maintain their spaced apart relationship, and
  - a pair of resilient ribbon electrodes, including said at least one electrode, secured to respective ones of said spaced apart strips.

16. The electrode assembly of claim 15, wherein:
said bridge connection joins said pair of strips at said edge unattached to said lead.

17. The electrode assembly of claim 15, wherein:
said bridge connection joins said pair of strips at a location between said attached and unattached edges thereof.

18. An electrode assembly for a lead to be installed on a patient's nerve, comprising:
- a thin, resilient, curled electrically insulating carrier having a split circumferential configuration longitudinally attached to and projecting generally perpendicularly from said lead at the distal end thereof,
- at least one resilient ribbon electrode secured to the underside of said carrier and electrically connected to an electrical conductor in said lead, and
- a selectively separable fastener for securing the split configuration of the carrier together to prevent separation from the nerve after installation of the electrode assembly onto the nerve,
- said split circumferential configuration comprising:
  - a curled rectangular loop attached substantially centrally to said lead and having substantially symmetrical portions projecting in opposite directions from said lead with confronting spaced apart edges, and
  - a pair of resilient ribbon electrodes, including said at least one electrode, secured to respective spaced apart legs of said rectangular loop projecting perpendicularly from said lead.

19. An electrode assembly for a lead to be installed on a patient's nerve, comprising:
- a thin, resilient, curled electrically insulating carrier having a split circumferential configuration longitudinally attached to and projecting generally perpendicularly from said lead at the distal end thereof,
- at least one resilient ribbon electrode secured to the underside of said carrier and electrically connected to an electrical conductor in said lead, and
- a selectively separable fastener for securing the split configuration of the carrier together to prevent separation from the nerve after installation of the electrode assembly onto the nerve, said selectively separable fastener comprising a flexible strap in combination with a fixed coupling, attached adjacent to opposite ones of split ends of said circumferential configuration of said carrier.

20. An electrode assembly for a lead to be installed on a patient's nerve, comprising:
- a thin, resilient, curled electrically insulating carrier having a split circumferential configuration longitudinally attached to and projecting generally perpendicularly from said lead at the distal end thereof,
- at least one resilient ribbon electrode secured to the underside of said carrier and electrically connected to an electrical conductor in said lead, and
- a selectively separable fastener for securing the split configuration of the carrier together to prevent separation from the nerve after installation of the electrode assembly onto the nerve,
- said lead including tear away webbing secured between adjacent serpentine segments of the lead in proximity to said carrier to enable lengthening of the lead in response to normal movements or growth of the patient's body.

* * * * *